(12) United States Patent
Jach et al.

(10) Patent No.: US 6,395,160 B1
(45) Date of Patent: May 28, 2002

(54) SENSOR FOR ANALYZING GASES

(75) Inventors: Olaf Jach, Boeblingen; Lothar Diehl, Stuttgart, both of (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/510,755

(22) Filed: Feb. 22, 2000

(30) Foreign Application Priority Data

Feb. 19, 1999 (DE) .......................................... 199 06 908

(51) Int. Cl.$^7$ ............................................ G01N 27/407
(52) U.S. Cl. ...................... 204/427; 204/425; 204/426
(58) Field of Search ................... 204/421–429

(56) References Cited

U.S. PATENT DOCUMENTS

| 4,207,159 A | * | 6/1980 | Kimura et al. ............... 204/425 |
| 4,502,939 A | * | 3/1985 | Holfelder et al. ............ 204/425 |
| 4,647,364 A | * | 3/1987 | Mase et al. .................. 204/428 |
| 5,290,421 A | * | 3/1994 | Reynolds et al. ........... 204/428 |
| 5,474,665 A | * | 12/1995 | Friese et al. ................. 204/426 |

OTHER PUBLICATIONS

H.–M. Wiedenmann et al., "Chapter 6: Exhaust Gas Sensors", Automotive Electronics Handbook, 6.1–6.23 (1994) month unavailable.

\* cited by examiner

*Primary Examiner*—T. Tung
(74) *Attorney, Agent, or Firm*—Kenyon & Kenyon

(57) ABSTRACT

A sensor for determining gas components and/or gas concentrations in gag mixtures, in particular, in the exhaust gas of an internal combustion engine, includes an inner pump electrode, an inner pump electrode supply conductor, a measuring electrode and a measuring electrode supply conductor. The inner electrode and the measuring electrode are in contact with the measuring area. In addition, separation is maintained between the measuring electrode supply conductor and the inner pump electrode supply conductor at least in the hot area of the sensor. At least in the hot area at least one of the electrode supply conductors is in contact with at least one oxygen reservoir, there being an at least largely gas-tight barrier between this and the measuring area. Furthermore, a sensor may include an inner pump electrode and an outer pump electrode, an inner pump electrode supply conductor and an outer pump electrode supply conductor, separation being maintained between them by a solid electrolyte foil, the outer pump electrode supply conductor being in contact at least in some areas with an oxygen reservoir. The design features of the two sensors may also be implemented in one sensor.

16 Claims, 3 Drawing Sheets

SENSOR FOR ANALYZING GASES

FIELD OF THE INVENTION

The present invention relates to a sensor for analyzing gases.

BACKGROUND INFORMATION

Sensors used to analyze the exhaust gas of internal combustion engines are described in Automotive Electronics Handbook (1994), Chapter 6, Wiedenmann et al., "Exhaust Gas Sensors". However, with these sensors, the problem of overswings or counterswings taking place when a jump response is carried out following a gas change procedure occurs during operation, particularly at high oxygen pump loads. These overswings or counterswings are known as $\lambda=1$ ripple.

SUMMARY OF THE INVENTION

A gas sensor according to the present invention has an advantage in that the $\lambda=1$ ripple, i.e., the counterswings or overswings that may occur with a jump response to gas change procedures, is reduced so that the sensor signal can be generated more quickly and precisely and is subject to fewer fluctuations.

At least in the hot area of the sensor, the measuring electrode supply conductor and/or the inner pump electrode supply conductor are in contact with an oxygen reservoir that makes a sufficient quantity of oxygen available at all times; this prevents an oxygen shortage at an electrode supply conductor when the pump voltage is applied during operation of the sensor, which tends to cause a Nernst voltage with respect to the other electrode supply conductors due to the resulting concentration difference, which, in turn, significantly contributes to the $\lambda=1$ ripple.

To ensure the actual measuring area with which the inner pump electrode and the measuring electrode are in contact is not enlarged by the oxygen reservoir according to the present invention in an undesirable manner, this reservoir and the measuring area are separated by a gas-tight barrier in an advantageous manner.

Furthermore, instead of or in addition to the measuring electrode supply conductor and/or the inner electrode supply conductor being in contact with an oxygen reservoir, it is advantageous if the outer electrode supply conductor is in contact with an oxygen reservoir. This means oxygen shortages and the resulting disruptive Nernst voltages at the outer electrode supply conductor can be avoided.

In contrast, in the case of sensors known from the related art, foil binders ($ZrO_2$) or other foils that have been applied via a printing process, for example, form a gas-tight seal around the electrode supply conductors of the measuring electrode, the inner electrode and the outer electrode within the vitrified sensor element; as a result, any oxygen shortage cannot be offset.

It should be noted that a person skilled in the art would understand the "hot" area of the sensor to mean the area of the gas sensor which is exposed to the gas to be measured and in which, respectively, the measuring signal is generated; one would understand the "cold" area to mean the area of the electrode supply conductors that is exposed to much lower temperatures and makes little contribution to generating the measuring signal.

It is advantageous to use a hollow space which is in contact with the inner pump electrode supply conductor and/or the outer pump electrode supply conductor and/or the measuring electrode supply conductor as the oxygen reservoir. Herein, it is advantageous if the inner pump electrode supply conductor and the outer pump electrode supply conductor are both in contact with one, possibly the same, hollow space or oxygen reservoir.

Furthermore, it is advantageous if the outer electrode supply conductor is in contact with an oxygen reservoir, in some areas this supply conductor not being covered by the usual cover layer, so that the outer electrode supply conductor is in direct contact there with the ambient air or another oxygen-containing gas.

It is advantageous if the gas-tight barrier separating the measuring area from the oxygen reservoir is a barrier, in particular, a barrier that is composed of a $ZrO_2$ foil binder.

Instead of or in addition to a hollow space, it is advantageous if the oxygen reservoir takes the form of a porous material or is provided as a layer that is porous in at least some areas. To accomplish this, it is advantageous if the porous material is in at least some areas in contact with the measuring electrode supply conductor and/or the inner pump electrode supply conductor and/or the outer pump electrode supply conductor, in the form of one or a plurality of porous areas. It is advantageous if the porous area is part of a solid electrolyte foil that maintains separation between the electrode supply conductors. It is advantageous to use porous $ZrO_2$ or $Al_2O_3$ as the porous material for the porous area.

Furthermore, it is advantageous if the oxygen reservoir is in contact with at least one electrode supply conductor not only in some areas of the hot area of the sensor, but also in the cold area of the sensor.

DETAILED DESCRIPTION

Figure 1:
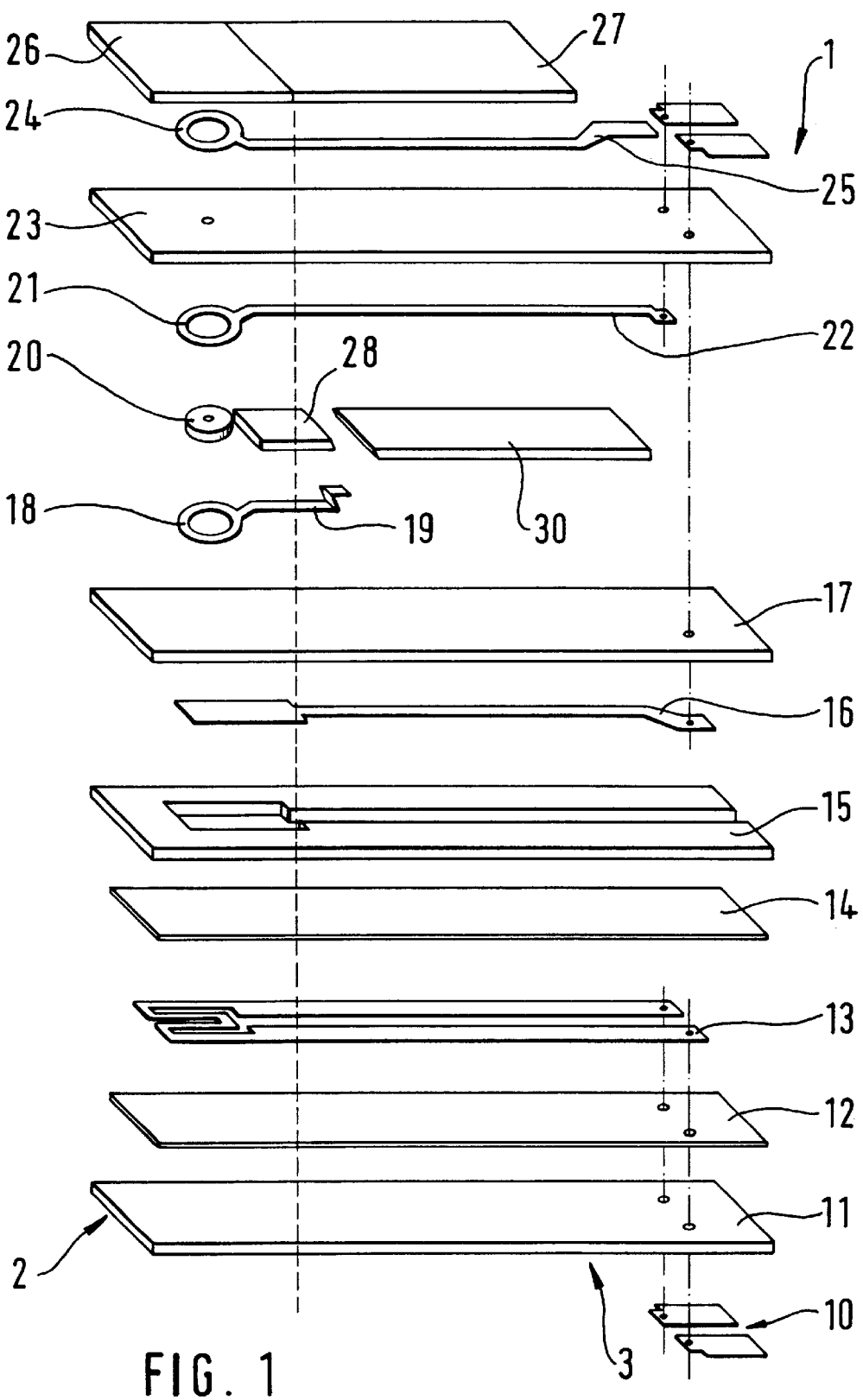
FIG. 1 shows an exploded view of a sensor known from the related art.

FIG. 1 shows an exploded view of a sensor for analyzing gases in the form of a planar sensor element 1 that is known per se from the related art. Sensor element 1 has a hot area 2 and a cold area 3. Furthermore, electrical terminal contacts 10, a heater foil 11, an insulating layer 12, a heater 13, a further insulating layer 14, a reference air channel foil 15 and a reference electrode 16 are provided. A first solid electrolyte foil 17, a measuring electrode 18 having a measuring electrode supply conductor 19, a diffusion barrier 20, an intermediate layer 28, a filler layer 30 and an inner pump electrode 21 having an inner pump electrode supply conductor 22 are provided above reference electrode 16. Inner pump electrode supply conductor 22 and measuring electrode supply conductor 19 come together in cold area 3 of the sensor. A second solid electrolyte foil 23, an outer pump electrode 24 having an outer pump electrode supply conductor 25, and a porous protective layer, this being an outer pump electrode cover layer 26 and an outer pump electrode supply conductor cover layer 27, are arranged above inner pump electrode 21.

Figure 2:
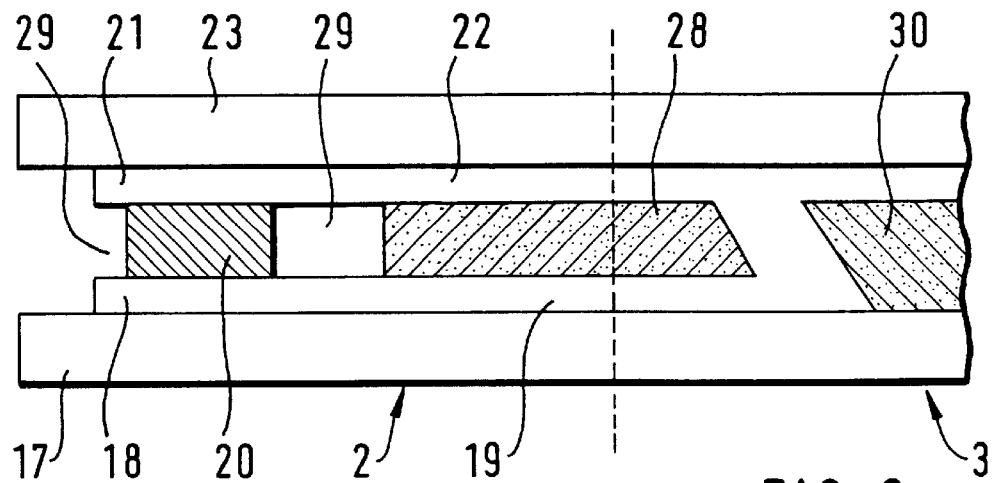
FIG. 2 shows a section through a partial area of the known sensor.

FIG. 2 shows a section through the known sensor shown in FIG. 1, along with additional details; only the area between solid electrolytes 17 and 23 and also only part of cold area 3 are shown. The broken line indicates where the area shown in FIG. 2 is located in FIG. 1. FIG. 2 goes beyond FIG. 1 in that it shows that in hot area 2 separation is maintained between inner pump electrode 21 and measuring electrode 18 so that measuring area 29 designed in the form of a hollow space that is in contact with the gas to be analyzed is formed. Intermediate layer 28 includes a $ZrO_2$ foil binder and maintains separation between electrode supply conductors 22 and 19 in hot area 2 and partly in cold area 3 as well. Further details concerning known sensor element 1 shown in FIGS. 1 and 2, e.g., the functioning of the individual components and layers, how they are specifically manufactured and the materials used, have not been provided because a person skilled in the art would know this.

Figure 3:
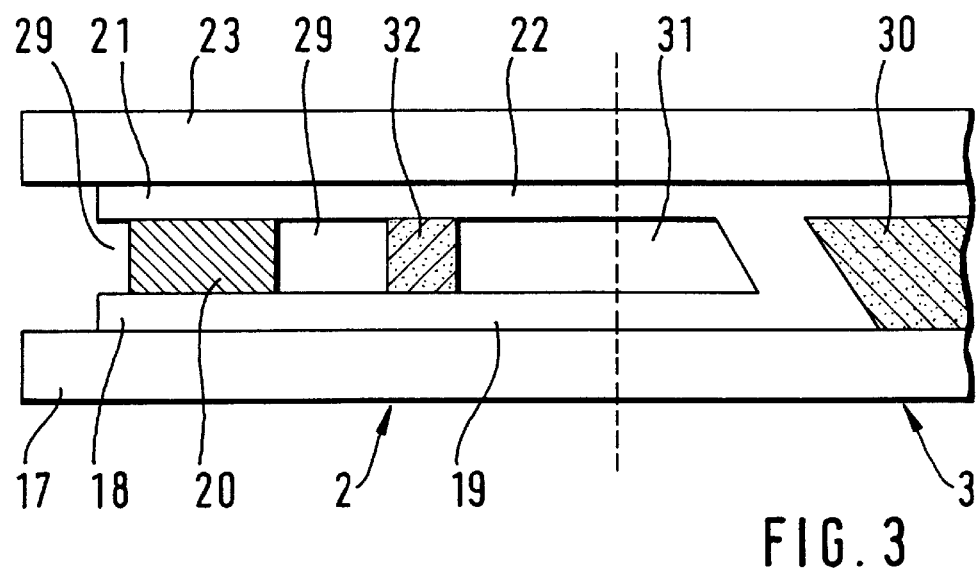
FIG. 3 shows a section through a partial area of a first embodiment of a sensor according to the present invention.

FIG. 3 shows a first exemplary embodiment of the present invention; in contrast with the known embodiment shown in FIG. 2, there is no intermediate layer 28, a separating barrier 32 and a hollow space 31, which is in contact with inner pump electrode supply conductor 22 and measuring electrode supply conductor 19, being provided instead. Separating barrier 32 is manufactured from a $ZrO_2$ foil binder which is applied via a printing process and subsequently vitrified, and forms an at least largely gas-tight barrier between hollow space 31 and measuring area 29, so that measuring area 29 is not enlarged. Hollow space 31 is used as an oxygen reservoir for preventing an oxygen shortage at electrode supply conductors 19 and 22. Hollow space 31 is manufactured as follows: when planar sensor element 1 is manufactured, a vitreous glass paste is applied at this location via a printing process; it then disintegrates during the subsequent vitrification process without leaving any residue, thus leaving hollow space 21.

Figure 4:
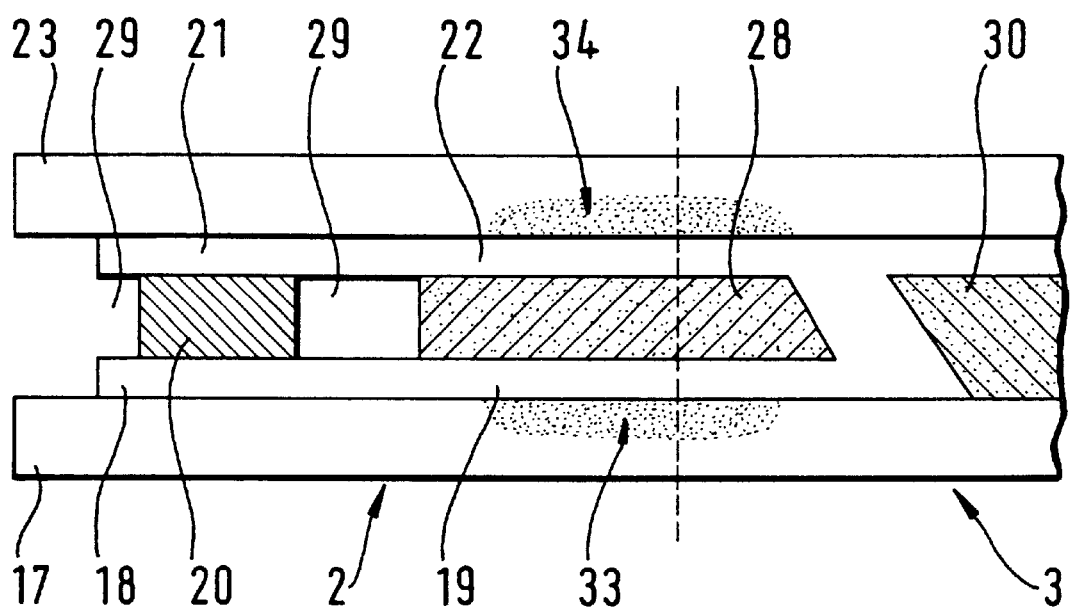
FIG. 4 shows a section through a partial area of a second embodiment of the sensor according to the present invention.

FIG. 4 shows a further exemplary embodiment of the present invention; in contrast with the known embodiment shown in FIG. 2, a first porous area 34 and a second porous area 33 are provided, which at least in hot area 2 are in contact with inner pump electrode supply conductor 22 and measuring electrode supply conductor 19, respectively, in some areas. Herein, first and second porous areas 33, 34 form an area on second solid electrolyte foil 23 and first solid electrolyte foil 17, respectively. Porous areas 33, 34 are able to absorb and store much more gas and thus, in particular, much more oxygen than solid electrolyte foils 17 and 23, and thus function as an oxygen reservoir when the sensor is in operation. Porous areas 33 and 34 are manufactured, for example, as follows: a porous $Al_2O_3$ or $ZrO_2$ layer is applied at this location via a printing process, or a porous area of solid electrolyte foils 17, 23 is created. A person skilled in the art would be familiar with further details as to how to manufacture porous areas 33 and 34, which can, for example, be created by making local changes in the proportion of organic binders in the solid electrolyte foils when printing processes are carried out in these areas.

The exemplary embodiments according to the present invention shown in FIG. 3 and FIG. 4 can also be combined so that hollow space 31 and porous areas 33 and 34 are in contact with electrode supply conductors 22 and 19. Furthermore, porous areas 33 and 34 can be provided below as well as above electrode supply conductors 22 and 19. According to further exemplary embodiments of the present invention, only second porous area 34 is provided and, at least in hot area 2, is in contact with inner pump electrode supply conductor 22; hollow space 31 is only in contact with inner pump electrode supply conductor 22, hollow space 31 being arranged above inner pump electrode supply conductor 22 or being an area of second solid electrolyte foil 23; or hollow space 31 is only in contact with measuring electrode supply conductor 19 and is arranged below measuring electrode supply conductor 19.

Further possible combinations, arrangements and versions, in particular, with respect to dimensioning and the number of hollow spaces 31 and/or porous area(s) 33 and 34 used as the oxygen reservoir, are contemplated by the present invention. However, it has been found to be advantageous if at least measuring electrode supply conductor 19 is in contact with an oxygen reservoir. According to a further exemplary embodiment of the present invention, the oxygen reservoir according to one of the preceding exemplary embodiments (implemented as a hollow space or porous area) extends from hot area 2 into cold area 3. To accomplish this, the oxygen reservoir may be designed as, for example, a longer hollow space or a more extended porous area.

As described above, one possible approach is to ensure there is contact between at least one of electrode supply conductors 19 or 22 and an oxygen reservoir; however, the present invention also contemplates that in some areas the oxygen reservoir is only in contact with outer pump electrode supply conductor 25. According to this exemplary embodiment, a third porous area is provided as the oxygen reservoir and, just as in the exemplary embodiments described above, includes at least one porous material such as $Al_2O_3$ or $ZrO_2$ and at least in some areas is implemented as a porous layer. This third porous area may be provided above or below outer pump electrode supply conductor 25. Furthermore, it may be implemented as a part or area of second solid electrolyte foil 23 or as a part or area of outer pump electrode supply conductor cover layer 27. This exemplary embodiment can be implemented in a particularly straightforward and useful way if outer pump electrode supply conductor cover layer 27 above outer pump electrode supply conductor 25 is removed in some areas or during the manufacturing process is not created in some areas, so that in these areas outer pump electrode supply conductor 25 is in direct contact with an oxygen-containing gas such as, for example, the ambient air. In this case the direct ambient air serves as the oxygen reservoir for outer electrode supply conductor 25.

Many different combinations of the exemplary embodiments described above are contemplated by the present invention. Thus, for example, an oxygen reservoir in the form of a third porous area that is in contact with outer pump electrode supply conductor 25 as well as an oxygen reservoir in the form of a hollow space 31, which is in contact with inner pump electrode supply conductor 22 and measuring electrode supply conductor 19, may be provided.

What is claimed is:

1. A sensor for determining at least one of gas components and gas concentrations in gas mixtures, comprising:

an inner pump electrode;

an inner pump electrode supply conductor being coupled to the inner pump electrode;

an outer pump electrode;

an outer pump electrode supply conductor being coupled to the outer pump electrode; and an oxygen reservoir, wherein a separation is maintained between (A) the inner pump electrode and the inner pump electrode supply conductor and (B) the outer pump electrode and the outer pump electrode supply conductor via a solid electrolyte foil, and wherein, in at least one area, the outer pump electrode supply conductor is in contact with the oxygen reservoir.

2. The sensor according to claim 1, wherein the sensor determines the at least one of gas components and gas concentrations in the gas mixtures in an exhaust gas of an internal combustion engine.

3. The sensor according to claim 1, wherein the oxygen reservoir is a hollow space.

4. The sensor according to claim 1, wherein the oxygen reservoir includes at least one porous material.

5. The sensor according to claim 4, wherein the at least one porous material includes a particular porous area, the particular porous area being in contact with the outer pump electrode in at least one area.

6. The sensor according to claim 4, wherein the at least one porous material includes at least one of (A) an at least largely porous $ZrO_2$ material and (B) an at least largely porous AlO material.

7. The sensor according to claim 1, wherein the oxygen reservoir is a layer having at least one porous area.

8. The sensor according to claim 1, wherein the oxygen reservoir extends into a cold area of the sensor.

9. The sensor according to claim 1, wherein, in at least one area, the outer pump electrode supply conductor is exposed directly to an oxygen-containing gas.

10. The sensor according to claim 1, wherein, in at least one area, the outer pump electrode supply conductor is exposed directly to air.

11. A sensor for determining at least one of gas components and gas concentrations in gas mixtures, comprising:

an inner pump electrode;

an inner pump electrode supply conductor being coupled to the inner pump electrode;

a measuring electrode, the measuring electrode and the inner pump electrode being in contact with a measuring area of the sensor;

a measuring electrode supply conductor being coupled to the measuring electrode, an outer pump electrode;

an outer pump electrode supply conductor being coupled to the outer pump electrode;

a first oxygen reservoir;

a second oxygen reservoir; and a gas tight barrier, wherein the gas-tight barrier is arranged between the first oxygen reservoir and the measuring area, wherein a first separation is maintained between the measuring electrode supply conductor and the inner pump electrode supply conductor at least in a hot area of the sensor, wherein a second separation is maintained between the inner pump electrode supply conductor and the outer pump electrode supply conductor via a solid electrolyte foil, wherein, in at least the hot area, at least one of the inner pump electrode supply conductor and the measuring electrode supply conductor is in contact with the first oxygen reservoir, and wherein, in at least one area, the outer pump electrode supply conductor is in contact with the second oxygen reservoir.

12. The sensor according to claim 11, wherein the sensor determines the at least one of gas components and gas concentrations in the gas mixtures in an exhaust gas of an internal combustion engine.

13. A sensor for determining at least one of gas components and gas concentrations in gas mixtures, comprising:

an inner pump electrode;

an inner pump electrode supply conductor being coupled to the inner pump electrode;

a measuring electrode, the measuring electrode and the inner pump electrode being in contact with a measuring area of the sensor;

a measuring electrode supply conductor being coupled to the measuring electrode;

at least one oxygen reservoir; and a gas tight barrier, wherein the gas tight barrier is arranged between the at least one oxygen reservoir and the measuring area, wherein a separation is maintained between the measuring electrode supply conductor and the inner pump electrode supply conductor at least in a hot area of the sensor, and wherein, in at least the hot area, the at least one oxygen reservoir is in contact with the measuring electrode supply conductor and the inner pump electrode supply conductor.

14. A sensor for determining at least one of gas components and gas concentrations in gas mixtures, comprising:

an inner pump electrode;

an inner pump electrode supply conductor being coupled to the inner pump electrode;

a measuring electrode, the measuring electrode and the inner pump electrode being in contact with a measuring area of the sensor;

a measuring electrode supply conductor being coupled to the measuring electrode;

at least one oxygen reservoir; and a gas tight barrier, wherein the gas tight barrier is arranged between the at least one oxygen reservoir and the measuring area, wherein a separation is maintained between the measuring electrode supply conductor and the inner pump electrode supply conductor at least in a hot area of the sensor, wherein, in at least the hot area, at least one of the inner pump electrode supply conductor and the measuring electrode supply conductor is in contact with the at least one oxygen reservoir, wherein the at least one oxygen reservoir includes at least one porous material, and wherein the at least one porous material includes at least one of a first porous area and a second porous area, the first porous area being in contact with the measuring electrode supply conductor in at least one area, the second porous area being in contact with the inner pump electrode supply conductor in at least one area.

15. A sensor for determining at least one of gas components and gas concentrations in gas mixtures, comprising:

an inner pump electrode;

an inner pump electrode supply conductor being coupled to the inner pump electrode;

a measuring electrode, the measuring electrode and the inner pump electrode being in contact with a measuring area of the sensor;

a measuring electrode supply conductor being coupled to the measuring electrode;

at least one oxygen reservoir; and a gas tight barrier, wherein the gas tight barrier is arranged between the at least one oxygen reservoir and the measuring area, wherein a separation is maintained between the measuring electrode supply conductor and the inner pump electrode supply conductor at least in a hot area of the sensor, wherein, in at least the hot area, at least one of the inner pump electrode supply conductor and the measuring electrode supply conductor is in contact with the at least one oxygen reservoir, wherein the at least one oxygen reservoir includes at least one porous material, and wherein the at least one porous material includes an area of a solid electrolyte foil.

16. A sensor for determining at least one of gas components and gas concentrations in gas mixtures, comprising:

an inner pump electrode;

an inner pump electrode supply conductor being coupled to the inner pump electrode;

a measuring electrode, the measuring electrode and the inner pump electrode being in contact with a measuring area of the sensor;

a measuring electrode supply conductor being coupled to the measuring electrode;

at least one oxygen reservoir; and a gas tight barrier, wherein the gas tight barrier is arranged between the at least one oxygen reservoir and the measuring area, wherein a separation is maintained between the measuring electrode supply conductor and the inner pump electrode supply conductor at least in a hot area of the sensor, wherein, in at least the hot area, at least one of the inner pump electrode supply conductor and the measuring electrode supply conductor is in contact with the at least one oxygen reservoir, wherein the at least one oxygen reservoir includes at least one layer having at least one porous area, and wherein the at least one porous area includes an area of a solid electrolyte foil.

* * * * *